United States Patent [19]

Anderson

[11] 4,197,842

[45] Apr. 15, 1980

[54] PORTABLE PULMONARY RESPIRATOR, INTERMITTENT POSITIVE PRESSURE BREATHING MACHINE AND EMERGENCY OXYGEN EQUIPMENT

[76] Inventor: Edmund M. Anderson, 535 Traffic Way, Arroyo Grande, Calif. 93420

[21] Appl. No.: 884,154

[22] Filed: Mar. 7, 1978

[51] Int. Cl.² .............................................. A61M 16/00
[52] U.S. Cl. ........................... 128/203.12; 128/204.19; 128/203.25; 128/205.25; 128/204.18
[58] Field of Search ............... 128/145.6, 145.5, 145.7, 128/145.8, 196, 197, 209, 210, DIG. 17, 188, 194

[56] References Cited

U.S. PATENT DOCUMENTS

| | | | |
|---|---|---|---|
| 3,319,627 | 5/1967 | Windsor | 128/145.8 X |
| 3,863,630 | 2/1975 | Cavallo | 128/145.6 |
| 3,990,442 | 11/1976 | Patneau | 128/145.6 X |

Primary Examiner—Henry L. Recla

[57] ABSTRACT

The invention provides a pulmonary respirator used in the treatment of such diseases as Pulmonary Emphysema, Asthma, Bronchitis and other respiratory diseases in addition to supplying emergency pure oxygen to the heart and airways of the patient.

Disclosed is a lightweight respirator, easily carried by a patient, having the appearance of a small piece of luggage, containing a bottle of oxygen under pressure, having a self-contained rechargeable battery pack for operation independently of external power, having a cigarette lighter plug-in connector for operation in an automobile or other vehicle wherein 12-volt D.C. current is available, and having, for operation independently of external power, a lightweight onboard battery pack which is automatically rechargeable while the respirator is being operated on either the 12-volt D.C. circuit or a 110 volt A.C. circuit.

The invention provides a control network which automatically selects the battery pack as the power source when either of the plug-in connections is in use.

A manual control assembly is provided, having a patient-controlled selector switch operable to provide blower operation for I.P.P.B. breathing or, alternatively, emergency oxygen breathing, cutting off the blower operation.

4 Claims, 2 Drawing Figures

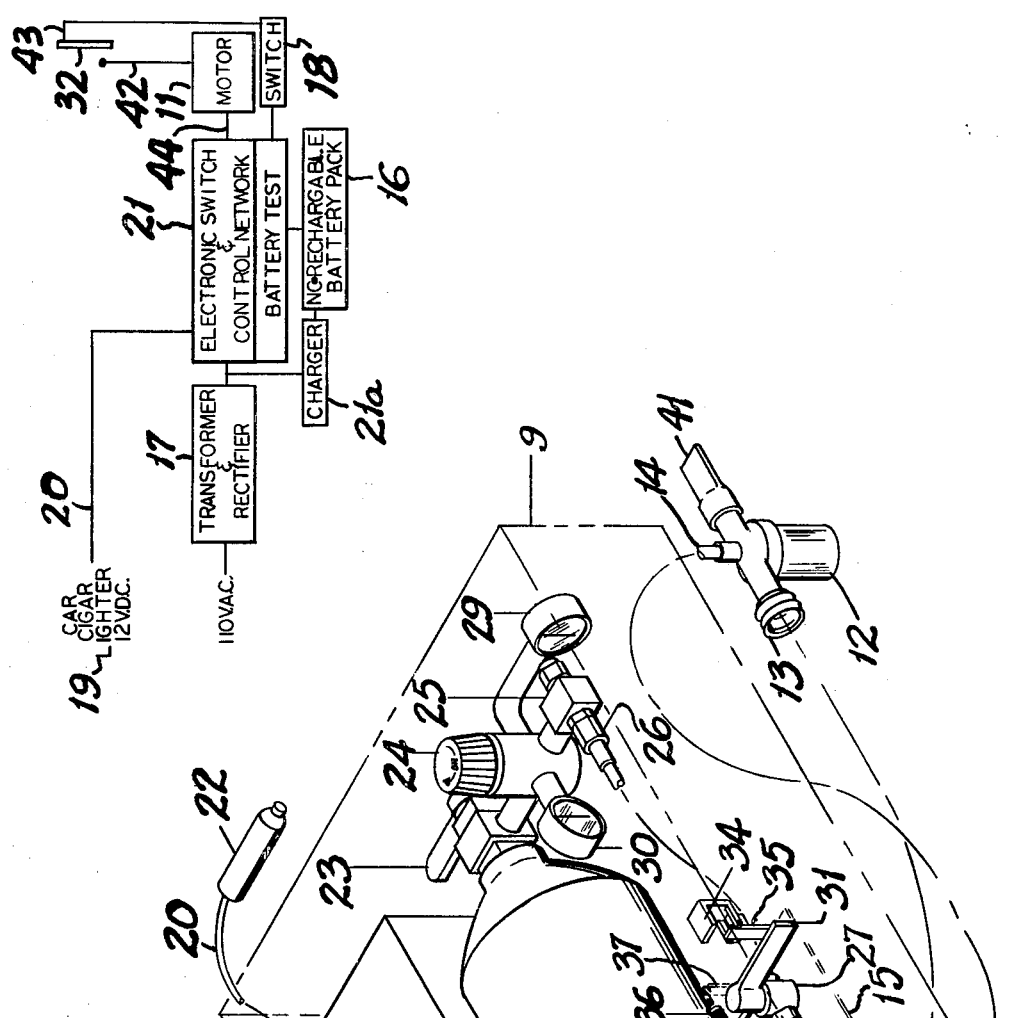

PORTABLE PULMONARY RESPIRATOR, INTERMITTENT POSITIVE PRESSURE BREATHING MACHINE AND EMERGENCY OXYGEN EQUIPMENT

BACKGROUND OF THE INVENTION

The patent to N.F. Beasley U.S. Pat. No. 3,221,733 discloses a pressure breathing therapy unit of the I.P.P.B. type, including a motor-driven air pump, a flow divider having branched outlets to a nebulizer supply conduit and to a flow and pressure regulator, and a nebulizer having a supply conduit and an automatic valve which opens during inspiration and closes at the beginning of expiration, bypassing the expired air through a relief valve.

The patent to Joseph Blasko U.S. Pat. No. 3,613,677 discloses a portable resuscitator including a carrying case, a pressurized oxygen bottle delivering through a pressure regulator to a bellows pump which, during an exhaust stroke, delivers oxygen to a face mask through a flexible hose and, during an intake stroke, draws oxygen from the bottle, the mask having a valve which closes during such intake stroke.

The patent to Ziermann, U.S. Pat. No. 3,379,194 discloses a respirator mounted in a carrying case, embodying a nebulizer which draws compressed air through a fluid amplifyer. The nebulizer provides medication where needed.

The patent to Enfield and Gandi, U.S. Pat. No. 3,874,379 discloses a nebulizer having a valve for facilitating inhalation of an aerosol by a patient and removal of exhaled gases from the patient.

SUMMARY OF THE INVENTION

The present invention provides an apparatus which is carried in a case by the patient, includes a bottle of oxygen, a battery-driven blower, and a patient operated switch movable to either of two positions, one of which provides for a mixture of air, oxygen and medication for I.P.P.B. breathing, and the other of which provides for pure oxygen intake, cutting off the blower. The apparatus also includes a 110 volt plug-in connection and electronic system for use in a home or building where 110 volt A.C. current is available, a cigarette lighter plug-in connection for use in an automobile, boat, airplane, etc. having a 12 volt D.C, outlet, and an electronic switching and control network having a micro-voltmeter responsive to a test button. A nebulizer is provided, having hose connections to the blower and to the oxygen bottle respectively, the oxygen supply being controlled by a patient-operated valve. When using pure oxygen, the nebulizer is replaced by a face mask and the valve handle is held in fully open position by a lock.

BRIEF DESCRIPTION OF THE DRAWINGS

FIG. 1 is a perspective view of the apparatus with the nebulizer attached in operative position, and FIG. 2 is a diagram of the switching and test unit.

Referring now to the drawing, a suitcase-type carrying case 9 encloses the operative mechanism which includes, in general, an oxygen bottle 10 capable of holding 396 liters of pure oxygen at 2015 P.S.I., an air blower 11, a nebulizer assembly 12 normally receiving air from the blower through a flexible tube 13 and oxygen from bottle 10 through an oxygen drive hose 14 controlled by a patient-operated valve assembly 15, a 12 volt D.C. battery pack 16 for driving the blower when other electric sources are not available, an electronic switching and control assembly 17 having a selector switch operated by a patient-controlled switch handle 18 which in one position provides for blower operation for I.P.P.B. breathing and in an alternate position cuts off the blower operation and provides for emergency pure oxygen supply to the valve assembly 15. A transformer and rectifier unit 21 (part of electronic assembly 17) is provided for converting household current supplied by a connection 19 to a 110 volt A.C. circuit, to 12 volt direct current suitable for driving the blower 11 and recharging battery pack 16 through a charger 21a; and a connector 22 is used for receiving 12 volt direct current from a cigar lighter outlet in an automotive vehicle during transportation, through a conduit 20.

An oxygen turn-on valve 23 controls the release of oxygen from bottle 10 through a regulator 24 and a safety valve 25 to an oxygen hose 26 and thence to a delivery valve 27, part of patient-controlled switching assembly 15, from which the oxygen is delivered to the nebulizer assembly 12 through the hose 14. A liter gage 29 and an oxygen contents gage 30 are included in the regulator assembly at the discharge end of oxygen bottle 10.

Switching assembly 15 includes the oxygen delivery valve 27, operated by a turn-on handle 31, an hermetically sealed reed switch 32 which is adapted to be operated to a conducting state by a magnet 33 carried by handle 31, a lock 34 mounted on a bracket 35 and adapted to frictionally engage and hold the end of handle 31 in the valve-opening and switch-closing position, and a coil spring 36 engaged under tension between a bracket projection 37 and the magnet-carrying arm 38 of turn-on handle 31, for holding the handle 31 in the valve-closing and circuit-opening position shown in the drawing.

Reed switch 32 is connected by means of conductors 42 and 43 to one side of blower motor 11 and to one side of the switch controlled by handle 18, the other side of motor 11 being connected, by a conductor 44, to electronic switch and control network 21.

The electronic switching and control network 17 includes a push-to-test button 39 and a micro-voltmeter 40 which indicates the voltage condition in the 12 V.D.C. circuit when depressed.

OPERATION

When switch handle 18 is in the "up" position, the control network 17 automatically selects the power source being used (the battery pack 16 when neither of the plug-in connections 19, 22 are operative, or one of the latter connections when plugged in) thus eliminating switching by hand. In order to test the batteries 16, the test button 39 is pushed. If the batteries are fully charged, the hand on meter 40 will move to the red zone; if it falls below the meter's red indicator, the 110 volt A.C. connector 19 is plugged into a conventional circuit outlet until the batteries are fully charged. With switch handle 18 in the "up" position, the circuit to blower 11 will be activated for I.P.P.B. breathing operation, using nebulizer assembly 12. The electronic switching unit 17 automatically cuts off the flow of oxygen during the expiration portion of the breathing cycle, and restores oxygen flow during inspiration. The patient-operated "on" handle 31, when pushed to breathe position, releases six liters of oxygen to nebulizer 12, creating a mist at mouthpiece 41 of the nebulizer assembly. A fraction of a second after the oxygen is released to the nebulizer, a magnetic field created by magnet 33 activates the sealed reed switch 32 which in turn starts the operation of blower 11 to push the medicinal mist to the patient's airways. The blower puts out a volume of air from zero to the equivalent of 27 centimeters of water (nine inches at top speed).

Following inhalation, the patient releases the "on" handle 31, which then returns to shut-off position, cutting off oxygen and power to the blower.

For pure oxygen breathing, the oxygen drive hose 14 is detached from oxygen valve 27, and a breathing face mask (not illustrated) with a hose attached, is connected to valve 27. The valve handle 18 of the electronic switching unit 17 is then moved downwardly to a position where the blower 11 is deenergized to cut off air flow, and pure oxygen will then be drawn through the face mask during each inspiration. The switching assembly 15 is operated as in the I.P.P.B. breathing, the handle 31 being locked in valve-opening position by lock 34. The doctor will set the regulator 24 to deliver the prescribed number of liters of oxygen, which will be read on gage 29.

I claim as my invention:

1. In combination:
   an oxygen bottle having a delivery outlet;
   an oxygen delivery valve communicating with said outlet to receive oxygen therefrom;
   a handle for operating said valve between open and closed positions, said handle having an arm carrying a magnet;
   a reed switch positioned to be closed by engagement thereof by said magnet in the open valve position of said handle;
   a blower electrically connected to and operated by closing of said reed switch;
   an air delivery tube connected at one end to the discharge outlet of said blower to receive air discharged therefrom, said tube having flexibility along its length;
   a nebulizer assembly operatively connected to the other end of said delivery tube to receive air therefrom when said handle is in said closed position; and
   a hose operatively connected between said oxygen delivery valve and said nebulizer assembly to receive oxygen from said bottle and to deliver it to said nebulizer assembly when said handle is in said open valve position;
   said nebulizer assembly including a patient's breathing mouthpiece for delivering the air or oxygen to a patient.

2. The apparatus of claim 1, said nebulizer assembly's operative connection to said blower being a flexible tube.

3. The apparatus of claim 1, including a step-down transformer having connections to said blower and to household power circuit for operating said blower when household current is available, and a rechargeable battery pack having a connection to said blower for operating said blower when household current is not available.

4. The apparatus of claim 1, including an electronic switching and control network assembly and a circuit including said blower, said reed switch and a double-throw switch operable, in one position, to energize said blower for normal I.P.P.B. breathing, and in another position, to deenergize said blower for pure oxygen breathing through said oxygen delivery valve.

* * * * *